United States Patent [19]
Ackermann et al.

[11] Patent Number: 6,001,992
[45] Date of Patent: Dec. 14, 1999

[54] ANTISENSE MODULATION OF NOVEL ANTI-APOPTOTIC BCL-2-RELATED PROTEINS

[75] Inventors: Elizabeth J. Ackermann, Solana Beach; C. Frank Bennett, Carlsbad; Nicholas M. Dean, Olivenhain; Eric G. Marcusson, San Diego, all of Calif.

[73] Assignee: Isis Pharmaceuticals Inc., Carlsbad, Calif.

[21] Appl. No.: 09/226,568

[22] Filed: Jan. 7, 1999

[51] Int. Cl.[6] .......................... C07H 21/04; C07H 21/02; A61K 48/00; C12Q 15/63; C12Q 1/68

[52] U.S. Cl. .................. 536/24.5; 536/23.1; 536/24.3; 435/91.1; 435/375; 435/6; 435/440; 514/44

[58] Field of Search .................. 435/325, 6, 91.1, 435/440; 536/24.5, 24.33, 24.3, 23.1; 514/44

[56] References Cited

U.S. PATENT DOCUMENTS

| | | | |
|---|---|---|---|
| 5,583,034 | 12/1996 | Green et al. | 435/240.2 |
| 5,646,008 | 7/1997 | Thompson et al. | 435/69.1 |
| 5,776,905 | 7/1998 | Gibbons et al. | 514/44 |

FOREIGN PATENT DOCUMENTS

| | | |
|---|---|---|
| 94/29330 | 12/1994 | WIPO . |
| 95/00642 | 1/1995 | WIPO . |
| 96/30513 | 10/1996 | WIPO . |
| 97/35971 | 10/1997 | WIPO . |
| 98/05777 | 2/1998 | WIPO . |

OTHER PUBLICATIONS

Andrea D. Branch, A good antisense molecule is hard to find, TIBS, 47–48, Feb. 1998.

Trisha Gura, Antisense Has Growing Pains, Science, pp. 575–577, Oct. 1995.

Stanley Crooke, Antisense '97: A roundtable on the state of the industry, Nature Biotechnology, p. 522, Jun. 1997.

Stanley Crooke, Antisense Research and Applications, Chapter 1, Basic Principles of Antisense Therapeutics, Springer–Verlag Press, Berlin, Heidelberg, New York, p. 3, Jul. 1998.

Uhlman et al., Antisense oligonucleotides: A New therapeutic principle, Chemical Reviews, vol. 90, No. 4, pp. 544–560, Jun. 1990.

Amarante–Mendes, et al., "Bcl–2–independent Bcr–Abl–mediated resistance to apoptosis: protection is correlated with up regulation of Bcl–$x_1$", *Oncogene* 1998 16, 1383–1390.

Chao, et al., "mcl–1 Is an Immediate Early Gene Activated by the Granulocyte–Macrophage Colony–Stimulating Factor (GM–CSF) Signaling Pathway and Is One Component of the Gm–CSF Viability Response", *Mole. Cell. Biol.* 1998 18, 4883–4898.

Fujio, et al., "Signals Through gp130 Upregulate bcl–x Gene Expression Via STAT1–binding cis–Element in Cardiac Myocytes", *J. Clin. Invest.* 1997 99, 2898–2905.

Pollman, et al., "Inhibition of neointimal cel bcl–x expression induces apoptosis and regression of vascular disease", *Nature Med.* 1998 4, 222–227.

Wang, et al., "Induction of bcl–x by CD40 Engagement Rescues slg–Induced Apoptosis in Murine B Cells[1]", *J. Immunol.* 1995 155, 3722–3725.

*Primary Examiner*—Nancy Degen
*Assistant Examiner*—Janet L Epps
*Attorney, Agent, or Firm*—Law Offices of Jane Massey Licata

[57] ABSTRACT

Compositions and methods are provided for modulating the expression of novel anti-apoptotic bcl-2-related proteins. Antisense oligonucleotides targeted to nucleic acids encoding the human novel anti-apoptotic bcl-2-related proteins A1 and mcl-1 are preferred. Methods of using these compounds for modulation of novel anti-apoptotic bcl-2-related protein expression and for treatment of diseases associated with expression of novel anti-apoptotic bcl-2-related proteins are also provided. Also provided are methods of using these compounds for promoting apoptosis and for treatment of diseases for which promotion of apoptosis is desired.

40 Claims, No Drawings

ANTISENSE MODULATION OF NOVEL ANTI-APOPTOTIC BCL-2-RELATED PROTEINS

FIELD OF THE INVENTION

The present invention provides compositions and methods for modulating the expression of novel anti-apoptotic bcl-2-related proteins. In particular, this invention relates to antisense compounds, particularly oligonucleotides, specifically hybridizable with nucleic acids encoding anti-apoptotic human bcl-2-related proteins. Such oligonucleotides have been shown to modulate the expression of novel anti-apoptotic bcl-2-related proteins.

BACKGROUND OF THE INVENTION

Programmed cell death, or apoptosis, is an essential feature of growth and development, as the control of cell number is a balance between cell proliferation and cell death. Apoptosis is an active rather than a passive process, resulting in cell suicide as a result of any of a number of external or internal signals. Apoptotic cell death is characterized by nuclear condensation, endonucleolytic degradation of DNA at nucleosomal intervals ("laddering") and plasma membrane blebbing. Programmed cell death plays an essential role in, for example, immune system development and nervous system development. In the former, T cells displaying autoreactive antigen receptors are removed by apoptosis. In the latter, a significant reshaping of neural structures occurs, partly through apoptosis.

An increasing number of genes and gene products have been implicated in apoptosis. One of these is bcl-2, which is an intracellular membrane protein shown to block or delay apoptosis. Overexpression of bcl-2 has been shown to be related to hyperplasia, autoimmunity and resistance to apoptosis, including that induced by chemotherapy (Fang et al., *J. Immunol.* 1994, 153, 4388–4398). A family of bcl-2-related genes has been described. All bcl-2 family members share two highly conserved domains, BH1 and BH2. bcl-2 family members include, but are not limited to, A1, mcl-1, bcl-w, bax, bad, bak and bcl-x. A1, mcl-1, bcl-w and bcl-xl (long form of bcl-x) are presently known to confer protection against apoptosis and are referred to herein as "anti-apoptotic bcl-2-related proteins." Of these, A1 and mcl-1 are known as "novel anti-apoptotic bcl-2-related proteins." In contrast, bax, bad, bak and bcl-xs (short form of bcl-x) are presently known to promote cell death by inhibiting this protective effect. The present invention relates to the novel anti-apoptotic human bcl-2-related proteins, particularly human A1 and mcl-1, and inhibition of the expression of these proteins using antisense technology.

The gene encoding A1 (also known as bcl-2-related gene expressed in fetal liver, or bfl-1, and Glasgow Rearranged Sequence, or GRS) was identified as an early response gene in murine hematopoietic cells treated with granulocyte-macrophage colony-stimulating factor. The human homolog was subsequently found to have extensive homology to bcl-2, especially within the BH1 and BH2 domains. A correlation was noted between the expression level of A1 and the development of stomach cancer in clinical samples. Choi et al., 1995, Oncogene 11, 1693–1698; WO 96/30513. The coding sequence of human A1 was cloned (Karsan et al., 1996, *Blood* 87, 3089–3096; Genbank accession no. U29680) and found to be expressed by hematopoietic cells but also a variety of nonhematopoietic tissues. A1 is rapidly inducible by phorbol esters and inflammatory cytokines, and possibly by vascular endothelial growth factor. A1 is believed to play a role in the regulation of physiological cell death during embryonic development. Carrio et al., 1996, *Am. J. Path.*, 149, 2133–2142. There is slight variation among A1 sequences, with the human A1 sequence originally defined as "GRS" differing by two amino acids from the A1 sequence originally defined as "bfl-1" The GRS sequence was originally isolated by NIH3T3 focus formation assay using DNA obtained from a patient with chronic myeloid leukemia. Kenny et al, *Oncogene* 14, 1997 997–1001. These researchers found a high level of A1 expression in the cancer cell lines U-937 (histiocytic lymphoma), HL-60 (promyelocytic leukemia) and Raji (Burkitt lymphoma) cells. Expression of A1 was also found in THP-1 (acute myeloid leukemia), BJAB (Burkitt lymphoma), activated Jurkat (acute T-cell leukemia) cells and K-562 erythroleukemia (CML blast crisis) cells.

mcl-1 was originally identified from the differentiating human myeloid leukemia cell line ML-1. Its expression was found to increase early in the induction or "programming" of differentiation of ML-1 cells before the appearance of differentiation markers. The coding region of mcl-1 was sequenced and found to have a pronounced region of sequence homology to bcl-2 in the carboxyl-terminal region. Kozopas et al., *Proc. Natl. Acad. Sci. USA.*, 1993, 90, 3516–3520; Genbank accession no. L08246. Unlike bcl-2, mcl-1 contains a strong PEST sequence (enriched in proline, glutamic acid, serine and threonine) which is present in a variety of proteins that undergo rapid turnover.

Overexpression of exogenously introduced mcl-1 has been shown to cause a prolongation of viability under conditions that normally cause apoptotic cell death, such as exposure to cytotoxic agents (the chemotherapeutic agent etoposide, calcium ionophore or UV irradiation) or the withdrawal of required growth factors. Zhou et al., *Blood* 89, 1997, 630–643.

Diseases and conditions in which apoptosis has been implicated fall into two categories, those in which there is increased cell survival (i.e., apoptosis is reduced) and those in which there is excess cell death (i.e., apoptosis is increased). Diseases in which there is an excessive accumulation of cells due to increased cell survival include cancer, autoimmune disorders and viral infections. Until recently, it was thought that cytotoxic drugs killed target cells directly by interfering with some life-maintaining function. However, of late, it has been shown that exposure to several cytotoxic drugs with disparate mechanisms of action induces apoptosis in both malignant and normal cells. Manipulation of levels of trophic factors (e.g., by anti-estrogen compounds or those which reduce levels of various growth hormones) has been one clinical approach to promote apoptosis, since deprivation of trophic factors can induce apoptosis. Apoptosis is also essential for the removal of potentially autoreactive lymphocytes during development and the removal of excess cells after the completion of an immune or inflammatory response. Recent work has clearly demonstrated that improper apoptosis may underlie the pathogenesis of autoimmune diseases by allowing abnormal autoreactive lymphocytes to survive. For these and other conditions in which insufficient apoptosis is believed to be involved, promotion of apoptosis is desired. Inhibition of novel anti-apoptotic bcl-2-related proteins according to the present invention is believed to result in promotion of apoptosis.

In the second category, AIDS and neurodegenerative disorders like Alzheimer's or Parkinson's disease represent disorders for which an excess of cell death due to promotion of apoptosis (or unwanted apoptosis) has been implicated.

Amyotrophic lateral sclerosis, retinitis pigmentosa, and epilepsy are other neurologic disorders in which apoptosis has been implicated. Apoptosis has been reported to occur in conditions characterized by ischemia, e.g. myocardial infarction and stroke. Apoptosis has also been implicated in a number of liver disorders including obstructive jaundice and hepatic damage due to toxins and drugs. Apoptosis has also been identified as a key phenomenon in some diseases of the kidney, i.e. polycystic kidney, as well as in disorders of the pancreas including diabetes (Thatte, et al., Drugs, 1997, 54, 511–532). For these and other diseases and conditions in which unwanted apoptosis is believed to be involved, inhibitors of apoptosis are desired.

Antisense oligonucleotides have been used to elucidate the role of several members of the bcl-2 family. Extensive studies using antisense oligonucleotides targeted to bcl-2 have been performed, and an antisense compound (G3139, Genta Incorporated) targeted to human bcl-2 has entered clinical trials for lymphoma and prostate cancer.

Amarante-Mendes et al., Oncogene, 1998, 16, 1383–1390, disclose antisense oligonucleotides targeted to bcr and bcl-x. The latter downregulated the expression of bcl-xl and increased the susceptibility of HL-60 Bcr-Abl cells to staurosporine.

U.S. Pat. No. 5,583,034 (Green et al.) discloses antisense oligonucleotides which hybridize to the nucleic acid sequence of an anti-apoptotic gene, preferably to the translation start site of bcr-abl.

Wang et al. used a phosphorothioate oligonucleotide targeted to the bcl-x translation start site to block CD40L-mediated apoptotic rescue in murine WEHI-231 lymphoma cells (J. Immunol., 1995, 155, 3722–3725).

Fujio et al. have used an antisense oligodeoxynucleotide targeted to murine and rat bcl-x mRNA to reduce bcl-xl protein expression (J. Clin. Invest., 1997, 99, 2898–2905). The compound tested was the same as that of Wang et al. Oligonucleotide treatment inhibited the cytoprotective effect of leukemia inhibitory factor in mouse or rat cardiac myocytes.

Pollman et al. used antisense oligodeoxynucleotides with phosphorothioate backbones to downregulate bcl-xl expression in blood vessel intimal cells (Nature Med., 1998, 4, 222–227). This resulted in induction of apoptosis and regression of vascular lesions. Antisense sequences were targeted to the translation initiation codon of mouse/human bcl-x (conserved sequence) and were used in rabbits. Gibbons et al., U.S. Pat. No. 5,776,905, disclose methods for targeted deletion of intimal lesion cells in the vasculature of a mammal with vascular disease, preferably with antisense molecules specific for anti-apoptotic genes, more preferably bcl-x and most preferably bcl-xl.

Thompson et al., U.S. Pat. No. 5,646,008 and WO 95/00642 describe an isolated and purified polynucleotide that encodes a polypeptide other than bcl-2 that promotes or inhibits programmed vertebrate cell death. Preferably the polypeptide is bcl-xl, bcl-xs or bcl-$x_1$. Polypeptides, polynucleotides identical or complementary to a portion of the isolated and purified polynucleotide, expression vectors, host cells, antibodies and therapeutic and diagnostic methods of use are also provided.

Yang et al., WO 98/05777 disclose bcl-xγ (gamma), a novel isoform of the bcl-x family which includes an ankyrin domain. Polypepticde and nucleic acid sequences for this isoform are disclosed, as well as, inter alia, methods for modulating bcl-xγ activity, including antisense methods.

Chao et al., Molec. Cell. Biol., 1998, 18, 4883–4898, used an antisense construct containing the entire human mcl-1 cDNA in antisense orientation to show that down-regulation of endogenous mcl-1 in TF-1 cells can induce apoptosis of these cells.

Cory et al. (WO 97/35971) disclose methods for modulating expression of bcl-w in a mammal by contacting the bcl-w gene with an effective amount of a modulator of bcl-w expression. Both enhanced and decreased bcl-w expression, including use of antisense sequences to bcl-w, are disclosed.

WO 96/30513 (Shin et al.) discloses the sequence of a Bcl-2 related gene, Bfl-1, and use of a Bcl-2 related gene for diagnosing cancer.

WO 94/29330 discloses, inter alia, the mcl-1 polypeptide sequence and polynucleotide sequence, host cells and vectors containing the latter, antibodies which bind to the mcl-1 polypeptide, and diagnostic and therapeutic methods using these compounds. Methods for treating a subject with a mcl-1 associated cell proliferative disorder are generally disclosed, including antisense oligonucleotide and ribozyme approaches. No specific sequence or targeting information is provided.

SUMMARY OF THE INVENTION

The present invention is directed to antisense compounds, particularly oligonucleotides, which are targeted to a nucleic acid encoding novel anti-apoptotic bcl-2-related proteins, and which modulate the expression of these family members. In preferred embodiments the antisense oligonucleotides are targeted to human A1 or human mcl-1. Pharmaceutical compositions comprising the antisense compounds of the invention are also provided. Further provided are methods of modulating the expression of novel anti-apoptotic bcl-2-related proteins in cells or tissues comprising contacting said cells or tissues with one or more of the antisense compounds or compositions of the invention. Methods for promoting apoptosis in cells or tissues are also provided. Further provided are methods of treating an animal, particularly a human, suspected of having or being prone to a disease or condition associated with expression of novel anti-apoptotic bcl-2-related proteins, or for which an increase in apoptosis is desired, by administering a therapeutically or prophylactically effective amount of one or more of the ant-isense compounds or compositions of the invention.

DETAILED DESCRIPTION OF THE INVENTION

The present invention comprehends antisense compounds capable of modulating expression of novel anti-apoptotic bcl-2-related proteins, particularly human A1 and mcl-1. A1 and mcl-1 inhibit apoptosis and therefore inhibitors of these targets are desired as promoters of apoptosis.

The present invention employs oligomeric antisense compounds, particularly oligonucleotides, for use in modulating the function of nucleic acid molecules encoding novel anti-apoptotic bcl-2-related proteins, ultimately modulating the amount of bcl-2-related protein produced. This is accomplished by providing antisense compounds which specifically hybridize with one or more nucleic acids encoding novel anti-apoptotic bcl-2-related proteins. As used herein, the terms "target nucleic acid" and "nucleic acid encoding a novel anti-apoptotic bcl-2-related protein" encompass DNA encoding a novel anti-apoptotic bcl-2-related protein, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the novel anti-apoptotic bcl-2-related protein. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a novel anti-apoptotic bcl-2-related protein. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particuLar set of conditions. In the context of the invention, "start codon" and "translation initiation codon" refer to the codon or codons that are used in vivo to initiate translation of an mRNA molecule transcribed from a gene encoding a novel anti-apoptotic bcl-2-related protein, regardless of the sequence(s) of such codons.

It is also known in the art that a translation termination codon (or "stop codon") of a gene may have one of three sequences, i.e., 5'-UAA, 5'-UAG ard 5'-UGA (the corresponding DNA csequences are 5'-TAA, 5'-TAG and 5'-TGA, respectively). The terms "start codon region" and "translation initiation codon region" refer to a portion of such an mRNA or gene that encompasses from about 25 to about 50 contiguous nuclec,tides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2'-, 3'- or 5'- hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure. However, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphorarnidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of EPNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N—alkyl; O—, S—, or N—alkenyl; O—, S— or N—alkynyl; or O—alkyl—O—alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2)_n$O]$_m$$CH_3$, O($CH_2)_n$O$CH_3$, O($CH_2$)$_n$$NH_2$, O($CH_2)_n$$CH_3$, O($CH_2)_n$O$NH_2$, and O($CH_2)_n$ON[($CH_2)_n$$CH_3$)$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes an alkoxyalkoxy group, 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504). A further preferred modification includes 2'-dimethylaminooxyethoxy, i.e., a O($CH_2)_2$ON($CH_3)_2$ group, also known as 2'-DMAOE.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cyt-osine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cyt-osine, 5-propynyl uracil and cytosine, 6-azo uracil, cytosineX and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The *Concise Encyclopedia Of Polymer Science And Engineering*, pp. 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Crooke, S. T., and Lebleu, B. eds., *Antisense Research and Applications*, CRC Press, Boca Raton, 1993, pp. 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, adenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. Nos.: 4,845,205; 5,130,–302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Mezd. Chem. Let.*, 993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al.,*Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937).

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleoticdes typically contain at least one region wherein the oligonucleotide is modified so as to confer upon the oligonucleotide increased resistance to nuclease degradation, increased cellular uptake, and/or increased binding affinity for the target nucleic acid. An additional region of the oligcnucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,378; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prcdrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 or in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred addition salts are acid salts such as the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embolic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesul fonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, umaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of one or more novel anti-apoptotic bcl-2-related proteins is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay inflammation or tumor formation, for example.

The antisense compounds of the invention are useful for research and diagnostics, because these compounds hybridize to nucleic acids encoding novel anti-apoptotic bcl-2-related proteins, enabling sandwich and other assays to easily be constructed to exploit this fact. Hybridization of the antisense oligonucleotides of the invention with a nucleic acid encoding a novel anti-apoptotic bcl-2-related protein can be detected by means known in the art. Such means may include conjugation of an enzyme to the oligonucleotide, radiolabelling of the oligonucleotide or any other suitable detection means. Kits using such detection means for detecting the level of novel anti-apoptotic bcl-2-related proteins in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Cligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91–192; Muranishi, *Critical Reviews in Therapeutic Drug Carrier Systems*, 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, 8:2, 91–192; Muranishi, *Critical Reviews in Therapeutic Drug Carrier Systems*, 1990, 7:1, 1–33; El-Hariri et al., *J. Pharm. Pharmacol.*, 1992, 44, 651–654). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used at concentrations of 03.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenecdiaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, 8:2, 92–192; Muranishi, *Critical Reviews in Therapeutic Drug Carrier Systems*, 1990, 7:1, 1–33; Buur et al., *J. Control Rel.*, 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, 8:2, 92–191); and perfluorochemical emulsions, such as FC-43 (Takahashi et al., *J. Pharm. Pharmacol.*, 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, 8:2, 92–191); and non-steroidal anti-inflammatory agents such as diclofenac sodium, indomethacin and phenylbutazone (Yamashita et al., *J. Pharm. Pharmacol.*, 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium st-earate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4 4,704,295; 4,556,552; 4,309,406; and 4,309,404, which are incorporated by reference.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.*, 1995, 6, 698–708).

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pp. 1206–1228. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pp. 2499–2506 and 46–49, respectively. Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 1()0 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis

Deoxy and 2'-alkoxy amidites

2'-Deoxy and 2'-methoxy beta-cyanoethyldiisopropyl phosphoramidites were purchased from commercial sources (e.g. Chemgenes, Needham, MA or Glen Research, Inc. Sterling, Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides, were synthesized according to published methods (Sanghvi, et. al., *Nucleic Acids Research*, 1993, 21, 3197–3203] using commercially available phosphoramidites (Glen Research, Sterling, Va. or ChemGenes, Needham, Mass.).

2'-Fluoro amidites

2'-Fluorodeoxyadenosine amidites

2'-fluoro oligonucleotides were synthesized as described previously by Kawasaki, et. al., *J. Med. Chem.*, 1993, 36, 831–841 and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid that was crushed to a light tan powder (57 g, 85% crude yield). The NMR spectrum was consistent with the structure, contaminated with phenol as its sodium salt (ca. 5%). The material was used as is for further reactions or purified further by column chromatography using a gradient of methanol in ethyl acetate (10–25%) to give a white solid, mp 222–4° C.

2'-O-Methoxyethyl-5-methyluridine 2,2$^1$-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 ml, of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazoie (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

2'-O-(dimethylaminooxyethyl) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O2-2-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40°C. The reaction mixture was flushed with argon and dry THF (369.8 mL, Aldrich, sure seal bottle) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-ethyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy) ethyl]-5-methyluridine as white foam (1.95, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (50%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl -N, N, N$^1$,N$^1$- tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 seconds and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphoDnate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. No. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378, 825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in 1M TBAF in THF for 24 hours at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl) Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.*, 1991, 266, 18162–18171. Results obtained with HPLC-purified material were similar to those obtained with non-HPLC purified material.

Example 7
Analysis of Oligonucleotide Inhibition of Novel Anti-apoptotic bcl-2-related Protein Expression Antisense modulation of novel anti-apoptotic bcl-2-related protein expression can be assayed in a variety of ways known in the art. For example, mRNA levels can be quantitated by Northern blot analysis, RNAse protection assay (RPA), competitive polymerase chain reaction (PCR), or real-time PCR (RT-PCR). RNA analysis can be performed on total cellular RNA or poly(A)+ mRNA. Methods of RNA isolation are taught in, for example, Ausubel, et al., *Current Protocols in Molecular Biology*, Volume 1, John Wiley & Sons, Inc., 1993, pp. 4.1.1–4.2.9 and 4.5.1–4.5.3. Northern blot analysis is routine in the art and is taught in, for example, Ausubel, et al., *Current Protocols in Molecular Biology*, Volume 1, John Wiley & Sons, Inc., 1996, pp. 4.2.1–4.2.9. Real-time quantitative (PCR) can be conveniently accomplished using the commercially 20 available ABI PRISM™ 7700 Sequence Detection System, available from PE-Applied Biosystems, Foster City, CA and used according to manufacturer's instructions. Other methods of PCR are also known in the art. Probes and primers are designed to hybridize to the target nucleic acid sequence, using published sequence information (for example, Genbank accession no. U29680 for human A1 and Genbank accession no. L08246 for human mcl-1.

Novel anti-apoptotic bcl-2-related protein levels can be quantitated in a variety of ways well known in the art, such as immunoprecipitation, Western blot analysis (immunoblotting), ELISA, flow cytometry or fluorescence-activated cell sorting (FACS). Antibodies directed to bcl-2-related proteins can be identified and obtained from a variety of sources, such as PharMingen Inc., San Diego Calif., or can be prepared via conventional antibody generation methods. Methods for preparation of polyclonal antisera are taught in, for example, Ausubel, et al., *Current Protocols in Molecular Biology*, Volume 2, John Wiley & Sons, Inc., 1997, pp. 11.12.1–11.12.9. Preparation of monoclonal antibodies is taught in, for example, Ausubel, et al., *Current Protocols in Molecular Biology*, Volume 2, John Wiley & Sons, Inc., 1997, pp. 11.4.1–11.11.5.

Immunoprecipitation methods are standard in the art and can be found at, for example, Ausubel, et al., *Current Protocols in Molecular Biology*, Volume 2, John Wiley & Sons, Inc., 1998, pp. 10.16.1–10.16.11. Western blot (immunoblot) analysis is standard in the art and can be found at, for example, Ausubel, et al., *Current Protocols in Molecular Biology*, Volume 2, John Wiley & Sons, Inc., 1997, pp. 10.8.1–10.8.21. Enzyme-linked immunosorbent assays (ELISA) are standard in the art and can be found at, for example, Ausubel, et al., *Current Protocols in Molecular Biology*, Volume 2, John Wiley & Sons, Inc., 1991, pp. 11.2.1–11.2.22.

Example 8
RNAse Protection Assay for Analysis of mRNA Levels

The ribonuclease (RNase) protection assay is a sensitive and specific method for quantitating expression levels (Zinn, et al., *Cell*, 1983, 34:865–79). The method is based on the hybridization of a target RNA to an in vitro transcribed $^{32}P$-labeled anti-sense RNA probe from a DNA template. RNase treatment follows, resulting in degradation of single-stranded RNA and excess probe. The probe and target RNA are resolved by denaturing polyacrylamide gel electrophoresis with the "protected" probe visualized using autoradiography or beta imaging equipment. Template sets can be purchased (PharMingen Inc., San Diego, Calif.) which contain a series of biologically relevant templates, each of distinct length and each representing a sequence in a distinct mRNA species. Each template set is capable of detecting up to 11 unique gene messages in a single reaction mix in addition to one or more housekeeping genes, L32 and GAPDH, which serve as internal controls. These template sets allow for multiple determinations to be made from a single sample. Multi-probe RPA can be performed on total RNA preparations derived by standard methods, without further purification of poly-A+ RNA.

Oligonucleotides were evaluated for their respective effects on mcl-1 mRNA levels along with total bcl-x mRNA 10 levels, using the RIBOQUANT™ RNase protection kit (Pharmingen, San Diego, Calif.). All assays were performed according to manufacturer's protocols. Briefly, multi-probe DNA template sets were used to generate antisense RNA transcripts radiolabeled with dUTP-$^{32}$P The template set used for apoptosis genes was the human hAPO-2 set. These radiolabeled probes were hybridized overnight with typically 10 μg of total cellular RNA. The reaction mixture was then digested with single-strand RNases to generate the protected fragments which were electrophoresed through a 5% acrylamide/urea gel. Protected bands were visualized and quantitated using a PhosphorImager (Molecular Dynamics, Sunnyvale, Calif.).

Example 9
Antisense Inhibition of Human A1 Expression—Phosphorothioate Oligodeoxynucleotides In accordance with the present invention, a series of oligonucleotides were designed to target human A1 RNA, using published sequences (Karsan et al., 1996, Blood 87, 3089–3096; Genbank Accession no. U29680, incorporated herein as SEQ ID NO: 1). The oligonucleotides are shown in Table 1.

(Stratagene, La Jolla, Calif.). Blots were hybridized for several hours with a single-stranded PCR $^{32}$P-labeled probe generated with a primer having the sequence AGAAGTAT-GTGTTGGCAATCGT (SEQ ID NO: 17) according to published methods. Bednarczuk, T. A. et al., BioTechniques, 1991, 10, 478. PCR was used to amplify nucleotides 22 to 684 of the A1 sequence. Northern blots were stripped and reprobed with random-primed $^{32}$P-labeled human G3PDH cDNA to confirm equivalent loading of RNA samples.

The results are shown in Table 1. As can be seen in the table, phosphorothioate oligodeoxynucleotides having SEQ ID NO: 4, 5, 7, 8, 9, 10, 11, 12, 13, 14 and 15 inhibited A1 mRNA expression by approximately 50% or more in this experiment. Of these, ISIS 17494 (SEQ ID NO: 13, targeting the stop codon) and ISIS 17495, SEQ ID NO: 14, targeting the 3' UTR just downstream of the stop codon, gave over 75% inhibition of A1 expression.

Example 10
Antisense Inhibition of A1 Expression—Mixed Backbone 2'-MOE Gapmer Oligonucleotides A second series of oligonucleotides targeted to human A1 was synthesized. The oligonucleotides are shown in Table 2.

TABLE 1

Antisense oligonucleotides targeted to human A1

| ISIS # | Sequence | Nucl. pos. | Target region | Chemistry | SEQ ID NO: | Activity (% of control) | % Inhib |
|---|---|---|---|---|---|---|---|
| 17483 | TGTGCTGAGAATGCTCACTC | 1 | 5'UTR | PS; deoxy; C = 5meC | 2 | 91 | 09 |
| 17484 | TTGAAGCTGTTGAGGCAATG | 19 | 5'UTR | PS; deoxy; C = 5meC | 3 | 55 | 45 |
| 17485 | AAGTCTTGAGCTGGCTCACC | 39 | 5'UTR | PS; deoxy; C = 5meC | 4 | 51 | 49 |
| 17486 | CTGTCATCTTCTGCCTGGTG | 66 | START CODON | PS; deoxy; C = 5meC | 5 | 49 | 51 |
| 17487 | CTGTAAATATATCCAAATTC | 91 | CODING | PS; deoxy; C = 5meC | 6 | 103 | — |
| 17488 | GCAGATAGTCCTGAGCCAGC | 111 | CODING | PS; deoxy; C = 5meC | 7 | 52 | 48 |
| 17489 | TGGACTGAGAACGCAACATT | 193 | CODING | PS; deoxy; C = 5meC | 8 | 40 | 60 |
| 17490 | AATAGTGTTCTGGCAGTGTC | 271 | CODING | PS; deoxy; C = 5meC | 9 | 44 | 56 |
| 17491 | TGATGCCGTCTTCAAACTCC | 309 | CODING | PS; deoxy; C = 5meC | 10 | 45 | 55 |
| 17492 | TGCTGTCGTAGAAGTTTCTT | 379 | CODING | PS; deoxy; C = 5meC | 11 | 48 | 52 |
| 17493 | TCACAGATCTTTCCTGTAAC | 556 | CODING | PS; deoxy; C = 5meC | 12 | 44 | 56 |
| 17494 | TGGAGTGTCCTTTCTGGTCA | 604 | STOP CODON | PS; deoxy; C = SmeC | 13 | 22 | 78 |
| 17495 | ATCGTTTCCATATCAGTCAG | 648 | 3'UTR | PS; deoxy; C = 5meC | 14 | 24 | 76 |
| 17496 | CAAAATTTCCATAACTCTGG | 724 | 3'UTR | PS; deoxy; C = 5meC | 15 | 36 | 64 |
| 17497 | CATACAATTTATTCATTACA | 750 | 3'UTR | PS; deoxy; C = 5meC | 16 | 69 | 31 |

"Nucl. pos." indicates the position of the first nucleotide on the target sequence (Genbank accession no. U29680; SEQ ID NO: 1) to which the oligonucleotide hybridizes.
"PS" = phosphorothioate linkage.
"5meC" = 5 - methylcytosine.
"Deoxy" = 2'-H.

Oligonucleotides were tested by Northern blot analysis in human umbilical vein endothelial cells (HUVEC) at a concentration of 100 nM. HUVECs were grown to 80% confluency and washed three times with pre-warmed (37° C.) Opto-MEM™ (Life Technologies, Inc., Gaithersburg, Md.). Oligonucleotides were premixed with 10 μg/ml Lipofectin™ reagent (Life Technologies, Inc., Gaithersburg, Md.) in Opti-MEM and applied to washed cells. Cells were incubated with oligonucleotide for 4 hr at 37° C. after which the medium was removed and replaced with fresh medium. Total cellular RNA was isolated using an RNeasy™ kit (Qiagen Inc., Valencia, Calif.). Isolated RNA was separated on a 1% agarose/formaldehyde gel, transferred to a Hybond N+ nylon membrane (Amersham, Arlington Heights, Ill.) overnight, and UV-crosslinked in a Stratalinker 2400

Target sites are indicated by nucleotide numbers, as given in the sequence source reference to which the oligonucleotide binds.

All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) in the deoxy gap and phosphodiester (P=O) in the wings. Cytidine residues throughout the molecule are 5-methylcytidines. Oligonucleotides were tested by Northern blot analysis as described in the previous example. Results are shown in Table 2.

TABLE 2

Gapped chimeric oligonucleotides targeted to A1

| ISIS # | Sequence | Nucl. pos. | Target region | Chemistry | SEQ ID NO: | Activity (% of control) | % Inhib |
|---|---|---|---|---|---|---|---|
| 17498 | TGTGCTGAGAATGCTCACTC | 1 | 5'UTR | 2'MOE/deoxy; PO/PS C = 5meC | 2 | 64 | 36 |
| 17499 | TTGAAGCTGTTGAGGCAATG | 19 | 5'UTR | 2'MOE/deoxy; PO/PS C = 5meC | 3 | 25 | 75 |
| 17500 | AAGTCTTGAGCTGGCTCACC | 39 | 5'UTR | 2'MOE/deoxy; PO/PS C = 5meC | 4 | 44 | 56 |
| 17501 | CTGTCATCTTCTGCCTGGTG | 66 | START CODON | 2'MOE/deoxy; PO/PS C = 5meC | 5 | 13 | 87 |
| 17502 | CTGTAAATATATCCAAATTC | 91 | CODING | 2'MOE/deoxy; PO/PS C = 5meC | 6 | N.D. | |
| 17503 | GCAGATAGTCCTGAGCCAGC | 111 | CODING | 2'MOE/deoxy; PO/PS C = 5meC | 7 | 24 | 76 |
| 17504 | TGGACTGAGAACGCAACATT | 193 | CODING | 2'MOE/deoxy; PO/PS C = 5meC | 8 | 16 | 84 |
| 17505 | AATAGTGTTCTGGCAGTGTC | 271 | CODING | 2'MOE/deoxy; PO/PS C = 5meC | 9 | 11 | 89 |
| 17506 | TGATGCCGTCTTCAAACTCC | 309 | CODING | 2'MOE/deoxy; PO/PS C = 5meC | 10 | 15 | 85 |
| 17507 | TGCTGTCGTAGAAGTTTCTT | 379 | CODING | 2'MOE/deoxy; PO/PS C = 5meC | 11 | 9.3 | 90.7 |
| 17508 | TCACAGATCTTTCCTGTAAC | 556 | CODING | 2'MOE/deoxy; PO/PS C = 5meC | 12 | 9.5 | 90.5 |
| 17509 | TGGAGTGTCCTTTCTGGTCA | 604 | STOP CODON | 2'MOE/deoxy; PO/PS C = 5meC | 13 | 6.7 | 93.3 |
| 17510 | ATCGTTTCCATATCAGTCAG | 648 | 3'UTR | 2'MOE/deoxy; PO/PS C = 5meC | 14 | 7.6 | 92.4 |
| 17511 | CAAAATTTCCATAACTCTGG | 724 | 3'UTR | 2'MOE/deoxy; PO/PS C = 5meC | 15 | 15 | 85 |
| 17512 | CATACAATTTATTCATTACA | 750 | 3'UTR | 2'MOE/deoxy; PO/PS C = 5meC | 16 | 22 | 78 |

"Nucl. pos." indicates the position of the first nucleotide on the target sequence (Genbank accession no. U29680; SEQ ID NO: 1) to which the oligonucleotide hybridizes.
"N.D." indicates no data available.
"PS" = phosphorothioate linkage;
"PO" = phosphodiester linkage.
"Deoxy" = 2'H;
"2'MOE" = 2'-O-methoxyethyl.
"5meC" = 5 - methylcytosine.

As 2'-MOE gapmers, SEQ ID NO: 3, 5, 7, 8, 9, 10, 11, 12, 13, 14, 15 and 16 gave over 75% reduction in A1 mRNA. Of these, SEQ ID NO: 11 (ISIS 17507), 12 (ISIS 17508), 13 (ISIS 17509) and 14 (ISIS 17510) gave over 90% reduction of A1 expression.

Dose-response experiments using ISIS 17510 (SEQ ID NO: 14, 2' MOE gapmer) gave an IC50 of less than 10 nM for A1 mRNA reduction using this compound.

Northern blot experiments using ISIS 17510 and a probe specific for the bcl-2 family member bcl-X demonstrated that the A1 antisense compound did not affect bcl-x mRNA levels.

Example 11
Antisense Inhibition of A1 Expression—Mixed Backbone 2'-MOE Hemimer Oligonucleotides A third series of oligonucleotides targeted to human A1 was synthesized. The oligonucleotides are shown in Table 3.

Target sites are indicated by nucleotide numbers, as given in the sequence source reference to which the oligonucleotide binds.

All compounds in Table 3 are chimeric "hemimer" oligonucleotides 20 nucleotides in length, composed of ten contiguous 2'-deoxynucleotides, joined to ten contiguous 2'-O-methoxyethyl (2'-MOE) nucleotides. The internucleoside (backbone) linkages are phosphorothioate (P=S) in the deoxy region and phosphodiester (P=O) in the 2'-MOE region. Cytidine residues throughout the molecule are 5-methylcytidines.

Oligonucleotides were tested by Northern blot analysis as described in previous examples. Results are shown in Table 3.

TABLE 3

"Hemimer" chimeric oligonucleotides targeted to A1

| ISIS # | Sequence | Nucl. pos. | Target region | Chemistry | SEQ ID NO: | Activity (% of control) | % Inhib |
|---|---|---|---|---|---|---|---|
| 17513 | TGTGCTGAGAATGCTCACTC | 1 | 5'UTR | Deoxy/2'MOE; PS/PO C = 5meC | 2 | 73 | 27 |
| 17514 | TTGAAGCTGTTGAGGCAATG | 19 | 5'UTR | Deoxy/2'MOE; PS/PO C = 5meC | 3 | 40 | 60 |
| 17515 | AAGTCTTGAGCTGGCTCACC | 39 | 5'UTR | Deoxy/2'MOE; PS/PO C = 5meC | 4 | 30 | 70 |
| 17516 | CTGTCATCTTCTGCCTGGTG | 66 | START CODON | Deoxy/2'MOE; PS/PO C = 5meC | 5 | 32 | 68 |
| 17517 | CTGTAAATATATCCAAATTC | 91 | CODING | Deoxy/2'MOE; PS/PO C = 5meC | 6 | 26 | 74 |
| 17518 | GCAGATAGTCCTGAGCCAGC | 111 | CODING | Deoxy/2'MOE; PS/PO C = 5meC | 7 | 32 | 68 |
| 17519 | TGGACTGAGAACGCAACATT | 193 | CODING | Deoxy/2'MOE; PS/PO C = 5meC | 8 | 32 | 68 |
| 17520 | AATAGTGTTCTGGCAGTGTC | 271 | CODING | Deoxy/2'MOE; PS/PO C = 5meC | 9 | 37 | 63 |
| 17521 | TGATGCCGTCTTCAAACTCC | 309 | CODING | Deoxy/2'MOE; PS/PO C = 5meC | 10 | 29 | 71 |
| 17522 | TGCTGTCGTAGAAGTTTCTT | 379 | CODING | Deoxy/2'MOE; PS/PO C = 5meC | 11 | 23 | 77 |
| 17523 | TCACAGATCTTTCCTGTAAC | 556 | CODING | Deoxy/2'MOE; PS/PO C = 5meC | 12 | 16 | 84 |
| 17524 | TGGAGTGTCCTTTCTGGTCA | 604 | STOP CODON | Deoxy/2'MOE; PS/PO C = 5meC | 13 | 8.5 | 91.5 |
| 17525 | ATCGTTTCCATATCAGTCAG | 648 | 3'UTR | Deoxy/2'MOE; PS/PO C = 5meC | 14 | 13 | 87 |
| 17526 | CAAAATTTCCATAACTCTGG | 724 | 3'UTR | Deoxy/2'MOE; PS/PO C = 5meC | 15 | 64 | 36 |
| 17527 | CATACAATTTATTCATTACA | 750 | 3'UTR | Deoxy/2'MOE; PS/PO C = 5meC | 16 | 47 | 53 |

"Nucl. pos." indicates the position of the first nucleotide on the target sequence (Genbank accession no. U29680; SEQ ID NO: 1) to which the oligonucleotide hybridizes.
"PS" = phosphorothioate linkage;
"PO" = phosphodiester linkage.
"Deoxy" = 2'H;
"2'MOE" = 2'-O-methoxyethyl.
"5meC" = 5 - methylcytosine.

As 2' MOE hemimers, SEQ ID NO: 11 (ISIS 17522), 12 (ISIS 17523), 13 (ISIS 17524) and 14 (ISIS 17525) gave at least 75% inhibition of A1 mRNA levels. Of these, ISIS 17524 (SEQ ID NO: 13) gave over 90% inhibition.

Example 12
Antisense Inhibition of Human mcl-1 Expression— Phosphorothioate 2'-moe Gapmer Oligonucleotides In accordance with the present invention, a series of oligonucleotides were designed to target human mcl-1 RNA, using published sequences (Kozopas et al., *Proc. Natl. Acad. Sci. USA.*, 1993, 90, 3516–3520, Genbank Accession No. L08246, incorporated herein as SEQ ID NO: 18). The oligonucleotides are shown in Table 4. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout. Cytidine residues throughout the molecule are 5-methylcytidines.

Oligonucleotides were tested by Northern blot analysis approximately as described in previous examples, using the human melanoma cell line C8161 (a gift of Dr. Dan Welch, Hershey Medical Center, Hershey, Pa.). Oligonucleotide (100 nM) and Lipofectin™ (10 μg/ml) were mixed and incubated for 30 minutes at room temperature. Cells were washed twice with Opti-MEM™, oligonucLeotide mixture was added and cells were incubated at 37° for 4 hours. Oligonucleotide was replaced with fresh medium (RPMI with 10% FCS). 24 hours later, RNA was isolated using the Rneasy™ kit (Qiagen, Valencia, Calif.). RNA was electrophoresed, transferred to nitrocellulose and probed with a random-primed mcl-1 EST probe (ATCC 1064916 I.M.A.G.E. Clone ID: 796506), obtained from the American Type Culture Collection (Manassas, Va.) and labeled with the Stripeasy™ kit (Ambion, Austin, Tex.).

Results are Shown in Table 4.

TABLE 4

Antisence oligonucleotides targeted to human mcl-1

| ISIS # | Sequence | Nucl. pos. | Target region | Chemistry | SEQ ID NO. | Activity (% of control) | % Inhib |
|---|---|---|---|---|---|---|---|
| 20404 | GCCAAACATTGCCAGTCGCC | 50 | | PS; 2'MOE/deoxy; C = 5meC | 19 | 83.2 | 16.8 |
| 20405 | AGCCAAAAGTCGCCCTCCCG | 152 | | PS; 2'MOE/deoxy; C = 5meC | 20 | 72.8 | 27.2 |
| 20406 | CTCGTACCCGTCCAGCTCCT | 431 | | PS; 2'MOE/deoxy; C = 5meC | 21 | 63.8 | 36.2 |
| 20407 | TGTTATTACCAGATTCCCCG | 501 | | PS; 2'MOE/deoxy; C = 5meC | 22 | 44.1 | 55.9 |
| 20408 | TTGGCTTTGTGTCCTTGGCG | 636 | | PS; 2'MOE/deoxy; C = 5meC | 23 | 38.4 | 61.6 |
| 20409 | GAGAGTCACAATCCTGCCCC | 842 | | PS; 2'MOE/deoxy; C = 5meC | 24 | 68.6 | 31.4 |
| 20410 | AAAGCCAGCAGCACATTCCT | 1045 | | PS; 2'MOE/deoxy; C = 5meC | 25 | 66.6 | 33.4 |
| 20411 | CCTCTTGCCACTTGCTTTTC | 1230 | | PS; 2'MOE/deoxy; C = 5meC | 26 | 77.7 | 22.3 |
| 20412 | CACAGGTCACTGGCATTCTT | 1519 | | PS; 2'MOE/deoxy; C = 5meC | 27 | 97.4 | 2.6 |
| 20413 | AAGAATCATGGAACCAAGCC | 1676 | | PS; 2'MOE/deoxy; C = 5meC | 28 | 84.1 | 15.9 |
| 20414 | CTCTCAATCCCAGGTTTTCA | 2091 | | PS; 2'MOE/deoxy; C = 5meC | 29 | 65.4 | 34.6 |
| 20415 | GGTCAAATGGAAGGAACTCA | 2231 | | PS; 2'MOE/deoxy; C = 5meC | 30 | 71.9 | 28.1 |
| 20416 | CAAATGTCTCTCCATCCACC | 2366 | | PS; 2'MOE/deoxy; C = 5meC | 31 | 37.5 | 62.5 |
| 20417 | AAATCCAAAGATGCCAATGC | 2564 | | PS; 2'MOE/deoxy; C = 5meC | 32 | 159.5 | — |
| 20418 | CAGTGCCAAAATCTAAAAGG | 2722 | | PS; 2'MOE/deoxy; C = 5meC | 33 | 87.5 | 12.5 |
| 20419 | CTTCCTCCCACCTCTCAATG | 2866 | | PS; 2'MOE/deoxy; C = 5meC | 34 | N.D. | |
| 20420 | GGCAGTTCTTCCCCATTACA | 3207 | | PS; 2'MOE/deoxy; C = 5meC | 35 | 43.8 | 56.2 |
| 20421 | ATTTGGCAGACAGGCTTTTA | 3391 | | PS; 2'MOE/deoxy; C = 5meC | 36 | 50.6 | 49.4 |
| 20422 | TAGACCACCTGCCTCCTCCT | 3591 | | PS; 2'MOE/deoxy; C = 5meC | 37 | 62.5 | 37.5 |
| 20423 | GTCCTAACCCTTCCTGGCAC | 3821 | | PS; 2'MOE/deoxy; C = 5meC | 38 | 68.8 | 31.2 |

"Nucl. pos." indicates the position of the first nucleotide on the target sequence (Genbank accession no. L08246; SEQ ID NO: 18) to which the oligonucleotide hybridizes.
"N.D." indicates no data available.
"PS" = phosphorothioate linkage;
"PO" = phosphodiester linkage.
"Deoxy" = 2'H;
"2'MOE" = 2'-O-methoxyethyl.
"5meC" = 5- methylcytosine.

SEQ ID NO: 22 (ISIS 20407), 23 (ISIS 20408), 31 (ISIS 20416), 35 (ISIS 20420), and 36 (ISIS 20421) inhibited mcl-1 mRNA levels by approximately 50% or more. Of these, ISIS 20408 and 20416 showed greatest reduction of mcl-1 expression.

A dose-response experiment was done using ISIS 20407, 20408 and 20416. RNAse protection assay was used to detect mcl-1 mRNA levels, using the hApo2 probe set (Pharmingen, San Diego, Calif.). ISIS 20407 demonstrated an IC50 of approximately 100 nM. ISIS 20408 and 20416 demonstrated IC50s of approximately 25 nM.

Example 13
Scid-human Leukemia Xenograft Model and Measurement of Apoptosis in Xenografts $10^7$ SEM-K2 cells in exponential phase of growth are injected subcutaneously into 8 SCID-NOD mice as a bolus (suspended in sterile saline). Engraftment and tumor formation occurs over a 2–3 week period. Micro Alzet pumps (Alza, Newark, Del) capable of delivering a continuous subcutaneous infusion over 14 days are used to deliver a dose of 100 µg per day (equivalent to 5 mg/kg) of antisense oligonucleotide into three animals. The remaining two animals received vehicle (sterile saline) only.

The expression of target protein measured in SEM-K2 cells from SCID-hu xenografts is measured using quantitative flow cytometry.

Xenografts are removed after sacrifice and mechanically dispersed into large volumes of medium. Leukocytes are purified by density gradient centrifugation and washed with medium before resuspending in 1 ml volumes at $1-5\times10^6$ cells/ml. Cells are incubated at 37° C. in 95% humidified air/5% $CO_2$ for 2 hours prior to induction of apoptosis with 20 µg/ml VP16 (Etoposidle) over 24 hours. Apoptosis is assessed nonspecifically using quantification of light scatter changes; reduction in side scatter (due to chromatin condensation) and reduction in forward scatter (due to cell shrinkage) are early changes associated with apoptosis. Bimodal population distributions consisting of apoptotic and non-apoptotic cells can be measured respectively allowing estimation of an apoptotic index for treated and negative control. Fold increase in apoptosis is calculated from their ratio. More specific determination of apoptosis is achieved using the Apo-Alert Caspase-3 Colorimetric Assay Kit (Clontech, Palo Alto, Calif.). This is a DEVD-specific caspase assay, a quantitative assay for the activity of caspase-3, a member of the caspase family thought to mediate apoptosis in most mammalian cell types. This assay utilizes a synthetic tetrapeptide, Asp-Glu-Val-Asp (DEVD) (SEQ ID NO: 39), labeled with either a fluorescent molecule, 7-amino-4-trifluoromethyl coumarin (AFC), or a colorimetric molecule, p-nitroanilide (pNA) as substrates. DEVD-dependent protease activity is assessed by detection of the free AFC or pNA cleaved from the substrates. Cell lysates are incubated with DEVD conjugated to paranitroanilide, a calorimetric substrate cleaved by CPP32 (caspase-3) and detectable using calorimetric spectrophotometry at 405 nm. The fold increase in $OD_{405nm}$ is used to determine the net VP16-induced apoptosis.

What is claimed is:

1. An antisense compound 8 to 30 nucleobases in length targeted to either SEQ ID NO: 1 or SEQ ID NO: 18, nucleic acid molecules encoding novel anti-apoptotic bcl-2-related proteins, wherein said antisense compound inhibits the expression of said novel anti-apoptotic bcl-2-related proteins.

2. The antisense compound of claim 1 which is an antisense oligonucleotide.

3. The antisense compound of claim 2 wherein the antisense oligonucleotide comprises at least one modified internucleoside linkage.

4. The antisense compound of claim 3 wherein the modified internucleoside linkage of the antisense oligonucleotide is a phosphorothioate linkage.

5. The antisense compound of claim 2 wherein the antisense oligonucleotide comprises at least one modified sugar moiety.

6. The antisense compound of claim 5 wherein the modified sugar moiety of the antisense oligonucleotide is a 2'-O-methoxyethyl sugar moiety.

7. The antisense compound of claim 2 wherein the antisense oligonucleotide comprises at least one modified nucleobase.

8. The antisense compound of claim 7 wherein the modified nucleobase is a 2'-O-methoxyethyl modified cytosine.

9. The antisense compound of claim 8 wherein the modified nucleobase of the antisense oligonucleotide is a 5-methylcytosine.

10. The antisense compound of claim 1 which is a chimeric oligonucleotide.

11. The antisense compound of claim 1 which is targeted to a nucleic acid encoding human A1.

12. The antisense compound of claim 1 which is targeted to a nucleic acid encoding human mcl-1.

13. A composition comprising the antisense compound of claim 1 and a carrier or diluent.

14. The composition of claim 13 further comprising a colloidal dispersion system.

15. A method of inhibiting the expression of a novel human anti-apoptotic bcl-2-related protein in human cells or tissues comprising contacting said cells or tissues in vitro with the antisense compound of claim 1 so that expression of said novel human anti-apoptotic bcl-2-related protein is inhibited.

16. The method of claim 15 wherein the antisense compound is targeted to a nucleic acid molecule encoding human A1.

17. The method of claim 15 wherein the antisense compound is targeted to a nucleic acid molecule encoding human mcl-1.

18. A method of promoting apoptosis in human cells or tissues comprising contacting said cells or tissues in vitro with the antisense compound of claim 1 so that expression of said novel human anti-apoptotic bcl-2-related protein is inhibited.

19. The method of claim 18 wherein the antisense compound is targeted to a nucleic acid molecule encoding human A1.

20. The method of claim 18 wherein the antisense compound is targeted to a nucleic acid molecule encoding human mcl-1.

21. An antisense compound up to 30 nucleobases in length targeted to a nucleic acid encoding human A1 wherein the antisense compound comprises at least 8 nucleobases of SEQ ID NO: 3, 4, 5, 6, 7, 8, 9, 10, 11, 12, 13, 14, 15 or 16, and inhibits expression of said human A1.

22. The antisense compound of claim 21 which is an antisense oligonucleotide.

23. The antisense compound of claim 22 wherein the antisense oligonucleotide comprises at least one modified internucleoside linkage.

24. The antisense compound of claim 23 wherein the modified internucleoside linkage of the antisense oligonucleotide is a phosphorothioate linkage.

25. The antisense compound of claim 22 wherein the antisense oligonucleotide comprises at least one modified sugar moiety.

26. The antisense compound of claim 25 wherein the modified sugar moiety of the antisense oligonucleotide is a 2'-O-methoxyethyl sugar moiety.

27. The antisense compound of claim 22 wherein the antisense oligonucleotide comprises at least one modified nucleobase.

28. The antisense compound of claim 27 wherein the modified nucleobase is a 2'-O-methoxyethyl modified cytosine.

29. The antisense compound of claim 28 wherein the modified nucleobase of the antisense oligonucleotide is a 5'-methylcytosine.

30. The antisense compound of claim 21 which is a chimeric oligonucleotide.

31. An antisense compound up to 30 nucleobases in length targeted to a nucleic acid encoding human mcl-1 wherein the antisense compound comprises at least 8 nucleobases of SEQ ID NO: 22, 23, 31, 35, or 36, and inhibits expression of said human mcl-1.

32. The antisense compound of claim 31 which is an antisense oligonucleotide.

33. The antisense compound of claim 32 wherein the antisense oligonucleotide comprises at least one modified internucleoside linkage.

34. The antisense compound of claim 33 wherein the modified internucleoside linkage of the antisense oligonucleotide is a phosphorothioate linkage.

35. The antisense compound of claim 32 wherein the antisense oligonucleotide comprises at least one modified sugar moiety.

36. The antisense compound of claim 35 wherein the modified sugar moiety of the antisense oligonucleotide is a 2'-O-methoxyethyl sugar moiety.

37. The antisense compound of claim 32 wherein the antisense oligonucleotide comprises at least one modified nucleobase.

38. The antisense compound of claim 37 wherein the modified nucleobase is a 2'-O-methoxyethyl modified cytosine.

39. The antisense compound of claim 38 wherein the modified nucleobase of the antisense oligonucleotide is a 5'-methylcytosine.

40. The antisense compound of claim 31 which is a chimeric oligonucleotide.

* * * * *

SEQUENCE LISTING

<160> NUMBER OF SEQ ID NOS: 39

<210> SEQ ID NO 1
<211> LENGTH: 780
<212> TYPE: DNA
<213> ORGANISM: Homo sapiens

<400> SEQUENCE: 1

```
gagtgagcat tctcagcaca ttgcctcaac agcttcaagg tgagccagct caagactttg      60
ctctccacca ggcagaagat gacagactgt gaatttggat atatttacag gctggctcag     120
gactatctgc agtgcgtcct acagatacca caacctggat caggtccaag caaaacgtcc     180
agagtgctac aaaatgttgc gttctcagtc caaaaagaag tggaaaagaa tctgaagtca     240
tgcttggaca atgttaatgt tgtgtccgta gacactgcca gaacactatt caaccaagtg     300
atggaaaagg agtttgaaga cggcatcatt aactgggaa gaattgtaac catatttgca     360
tttgaaggta ttctcatcaa gaaacttcta cgacagcaaa ttgccccgga tgtggatacc     420
tataaggaga tttcatattt tgttgcggag ttcataatga ataacacagg agaatggata     480
aggcaaaacg gaggctggga aaatggcttt gtaaagaagt ttgaacctaa atctggctgg     540
atgacttttc tagaagttac aggaaagatc tgtgaaatgc tatctctcct gaagcaatac     600
tgttgaccag aaaggacact ccatattgtg aaaccggcct aattttttctg actgatatgg     660 aaacgattgc caacacatac ttctactttt aaataaacaa ctttgatgat gtaacttgac     720
cttccagagt tatggaaatt ttgtccccat gtaatgaata aattgtatgt atttttctct     780
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 2

```
tgtgctgaga atgctcactc                                                   20
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 3

```
ttgaagctgt tgaggcaatg                                                   20
```

<210> SEQ ID NO 4
<211> LENGTH: 20

```
<212> TYPE: DNA
<213> ORGANISM: Artificial Sequence
<220> FEATURE:
<223> OTHER INFORMATION: Description of Artificial Sequence: antisense
      sequence

<400> SEQUENCE: 4
aagtcttgag ctggctcacc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 5
ctgtcatctt ctgcctggtg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 6
ctgtaaatat atccaaattc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 7
gcagatagtc ctgagccagc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 8
tggactgaga acgcaacatt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 9
aatagtgttc tggcagtgtc                                              20

<210> SEQ ID NO 10
<211> LENGTH: 20
<212> TYPE: DNA
<213> ORGANISM: Artificial Sequence
```

-continued

```
<220> FEATURE:
<223> OTHER INFORMATION: Description of Artificial Sequence: antisense
      sequence

<400> SEQUENCE: 10
tgatgccgtc ttcaaactcc                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 11
tgctgtcgta gaagtttctt                                                     20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 12
tcacagatct ttcctgtaac                                                     20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 13
tggagtgtcc tttctggtca                                                     20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 14
atcgtttcca tatcagtcag                                                     20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 15
caaaatttcc ataactctgg                                                     20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: antisense
```

-continued

<400> SEQUENCE: 16
catacaattt attcattaca          20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: antisense sequence

<400> SEQUENCE: 17
agaagtatgt gttggcaatc gt          22

<210> SEQ ID NO 18
<211> LENGTH: 3934
<212> TYPE: DNA
<213> ORGANISM: Homo sapiens
<220> FEATURE:
<223> OTHER INFORMATION: Description of Artificial Sequence: antisense sequence

<400> SEQUENCE: 18

| | | | | | |
|---|---|---|---|---|---|
| tccagtaagg | agtcggggtc | ttccccagtt | ttctcagcca | ggcggcggcg | gcgactggca | 60 |
| atgtttggcc | tcaaaagaaa | cgcggtaatc | ggactcaacc | tctactgtgg | ggggggccggc | 120 |
| ttggggggccg | gcagcggcgg | cgccacccgc | ccgggagggc | gacttttggc | tacgagaag | 180 |
| gaggcctcgg | cccggcgaga | gataggggga | ggggaggccg | gcgcggtgat | ggcggaagc | 240 |
| gccggcgcaa | gccccccgtc | caccctcacg | ccagactccc | ggagggtcgc | gcggccgccg | 300 |
| cccattggcg | ccgaggtccc | cgacgtcacc | gcgaccccg | cgaggctgct | tttcttcgcg | 360 |
| cccacccgcc | gcgcggcgcc | gcttgaggag | atggaagccc | cggccgctga | cgccatcatg | 420 |
| tcgcccgaag | aggagctgga | cgggtacgag | ccggagcctc | tcgggaagcg | gccggctgtc | 480 |
| ctgccgctgc | tggagttggt | cggggaatct | ggtaataaca | ccagtacgga | cgggtcacta | 540 |
| ccctcgacgc | cgccgccagc | agaggaggag | gaggacgagt | tgtaccggca | gtcgctggag | 600 |
| attatctctc | ggtaccttcg | ggagcaggcc | accggcgcca | aggacacaaa | gccaatgggc | 660 |
| aggtctgggg | ccaccagcag | gaaggcgctg | gagaccttac | gacgggttgg | ggatggcgtg | 720 |
| cagcgcaacc | acgagacggt | cttccaaggc | atgcttcgga | aactggacat | caaaaacgaa | 780 |
| gacgatgtga | atcgttgtc | tcgagtgatg | atccatgttt | tcagcgacgg | cgtaacaaac | 840 |
| tggggcagga | ttgtgactct | catttctttt | ggtgcctttg | tggctaaaca | cttgaagacc | 900 |
| ataaaccaag | aaagctgcat | cgaaccatta | gcagaaagta | tcacagacgt | tctcgtaagg | 960 |
| acaaaacggg | actggctagt | taaacaaaga | ggctgggatg | ggtttgtgga | gttcttccat | 1020 |
| gtagaggacc | tagaaggtgg | catcaggaat | gtgctgctgg | cttttgcagg | tgttgctgga | 1080 |
| gtaggagctg | gtttggcata | tctaataaga | tagccttact | gtaagtgcaa | tagttgactt | 1140 |
| ttaaccaacc | accaccacca | ccaaaaccag | tttatgcagt | tggactccaa | gctgtaactt | 1200 |
| cctagagttg | caccctagca | acctagccag | aaaagcaagt | ggcaagagga | ttatggctaa | 1260 |
| caagaataaa | tacatgggaa | gagtgctccc | cattgattga | agagtcactg | tctgaaagaa | 1320 |
| gcaaagttca | gtttcagcaa | caaacaaact | ttgtttggga | agctatggag | gaggactttt | 1380 |
| agatttagtg | aagatggtag | ggtggaaaga | cttaatttcc | ttgttgagaa | caggaaagtg | 1440 |
| gccagtagcc | aggcaagtca | tagaattgat | tacccgccga | attcattaat | ttactgtagt | 1500 |

-continued

```
agtgttaaga gaagcactaa gaatgccagt gacctgtgta aaagttacaa gtaatagaac   1560
tatgactgta agcctcagta ctgtacaagg gaagcttttc ctctctctaa ttagctttcc   1620
cagtatactt cttagaaagt ccaagtgttc aggactttta tacctgttat actttggctt   1680
ggttccatga ttcttacttt attagcctag tttatcacca ataatacttg acggaaggct   1740
cagtaattag ttatgaatat ggatatcctc aattcttaag acagcttgta aatgtatttg   1800
taaaaattgt atatatttt acagaaagtc tatttccttg aaacgaagga agtatcgaat   1860
ttacattagt tttttcata ccctttttgaa ctttgcaact tccgtaatta ggaacctgtt   1920
tcttacagct tttctatgct aaactttgtt ctgttcagtt ctagagtgta tacagaacga   1980
attgatgtgt aactgtatgc agactggttg tagtggaaca aatctgataa ctatgcaggt   2040 ttaaatttc ttatctgatt ttggtaagta ttccttagat aggttttctt tgaaaacctg   2100
ggattgagag gttgatgaat ggaaattctt tcacttcatt atatgcaagt tttcaataat   2160
taggtctaag tggagtttta aggttactga tgacttacaa ataatgggct ctgattgggc   2220
aatactcatt tgagttcctt ccatttgacc taatttaact ggtgaaattt aaagtgaatt   2280
catgggctca tctttaaagc ttttactaaa agattttcag ctgaatggaa ctcattagct   2340
gtgtgcatat aaaagatca catcaggtgg atggagagac atttgatccc ttgtttgctt   2400
aataaattat aaaatgatgg cttggaaaag caggctagtc taaccatggt gctattatta   2460
ggcttgcttg ttacacacac aggtctaagc ctagtatgtc aataaagcaa atacttactg   2520
ttttgtttct attaatgatt cccaaacctt gttgcaagtt tttgcattgg catctttgga   2580
tttcagtctt gatgtttgtt ctatcagact taaccttta tttcctgtcc ttccttgaaa   2640
ttgctgattg ttctgctccc tctacagata tttatatcaa ttcctacagc tttccctgc    2700 catccctgaa ctctttctag ccctttага ttttggcact gtgaaacccc tgctggaaac   2760
ctgagtgacc ctccctcccc accaagagtc cacagacctt tcatctttca cgaacttgat   2820
cctgttagca ggtggtaata ccatgggtgc tgtgacacta acagtcattg agaggtggga   2880
ggaagtccct tttccttgga ctggtatctt ttcaactatt gttttatcct gtctttgggg   2940
gcaatgtgtc aaaagtcccc tcaggaattt tcagaggaaa gaacatttta tgaggctttc   3000
tctaaagttt cctttgtata ggagtatgct cacttaaatt tacagaaaga ggtgagctgt   3060
gttaaacctc agagtttaaa agctactgat aaactgaaga aagtgtctat attggaacta   3120
gggtcatttg aaagcttcag tctcggaaca tgacctttag tctgtggact ccatttaaaa   3180
ataggtatga ataagatgac taagaatgta atggggaaga actgccctgc ctgcccatct   3240
cagagccata aggtcatctt tgctagagct attttttacct atgtatttat cgttcttgat   3300
cataagccgc ttatttatat catgtatctc taaggaccta aaagcacttt atgtagttt    3360 taattaatct taagatctgg ttacggtaac taaaagcctg tctgccaaat ccagtggaaa   3420
caagtgcata gatgtgaatt ggttttaagg ggccccactt cccaattcat taggtatgac   3480
tgtggaaata cagacaagga cttagttgat attttgggct tggggcagtg agggcttagg   3540
acaccccaag tggtttggga aaggaggagg gagtggtggg tttatagggg aggaggaggc   3600
aggtggtcta agtgctgact ggctacgtag ttcgggcaaa tcctccaaaa gggaaaggga   3660
ggatttgctt agaaggatgg ggctcccagt gactactttt tgacttctgt ttgtcttacg   3720
cttctctcag ggaaaaacat gcagtcctct agtgtttcat gtacattctg tgggggtga    3780 acaccttggt tctggttaaa cagctgtact tttgatagct gtgccaggaa gggttaggac   3840
caactacaaa ttaatgttgg ttgtcaaatg tagtgtgttt ccctaacttt ctgtttttcc   3900
```
tgagaaaaaa aaataaatct tttattcaaa taaa                                      3934

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 19
gccaaacatt gccagtcgcc                                                        20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 20
agccaaaagt cgccctcccg                                                        20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 21
ctcgtacccg tccagctcct                                                        20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 22
tgttattacc agattccccg                                                        20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 23
ttggctttgt gtccttggcg                                                        20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 24
gagagtcaca atcctgcccc                                                        20

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 25
aaagccagca gcacattcct                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 26
cctcttgcca cttgcttttc                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 27
cacaggtcac tggcattctt                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 28
aagaatcatg gaaccaagcc                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 29
ctctcaatcc caggttttca                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 30
ggtcaaatgg aaggaactca                                                    20

<210> SEQ ID NO 31
```

```
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 31
caaatgtctc tccatccacc                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 32
aaatccaaag atgccaatgc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 33
cagtgccaaa atctaaaagg                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 34
cttcctccca cctctcaatg                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 35
ggcagttctt ccccattaca                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 36
atttggcaga caggctttta                                               20

<210> SEQ ID NO 37
<211> LENGTH: 20
<212> TYPE: DNA
```

```
<213> ORGANISM: Artificial Sequence
<220> FEATURE:
<223> OTHER INFORMATION: Description of Artificial Sequence: antisense
      sequence

<400> SEQUENCE: 37
tagaccacct gcctcctcct                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 38
gtcctaaccc ttcctggcac                                                    20

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 39

Asp Glu Val Asp
```